United States Patent [19]

Lalonde

[11] Patent Number: 4,723,548
[45] Date of Patent: Feb. 9, 1988

[54] TENDON APPROXIMATOR

[76] Inventor: Donald H. Lalonde, Millidge Place, 705 Millidge Ave., Saint John, New Brunswick, Canada, E2K 2N7

[21] Appl. No.: 936,870

[22] Filed: Dec. 2, 1986

[30] Foreign Application Priority Data

Dec. 20, 1985 [CA] Canada ................................ 498394

[51] Int. Cl.$^4$ ................................................ A61B 17/08
[52] U.S. Cl. ..................................... 128/335; 128/346
[58] Field of Search ............... 128/335, 303 R, 334 R, 128/352, 346; 269/53

[56] References Cited

U.S. PATENT DOCUMENTS

| | | | |
|---|---|---|---|
| 2,796,867 | 6/1957 | Pearson | 128/346 |
| 3,561,448 | 2/1971 | Peternel | 128/346 |
| 3,911,926 | 10/1975 | Peters | 128/346 |
| 4,165,747 | 8/1979 | Bermant | 128/346 |
| 4,316,470 | 2/1982 | Braun et al. | 128/346 |
| 4,635,636 | 1/1987 | Goldstein | 128/346 |

Primary Examiner—Richard C. Pinkham
Assistant Examiner—Gary Jackson
Attorney, Agent, or Firm—Jordan and Hamburg

[57] ABSTRACT

There is provided a new and useful tendon approximator comprising a slide bar, a pair of needle arms mounted on the slide bar, at least one of which is slidably mounted for movement over a range of positions on the slide bar, each arm comprising an elongated member extending outwardly from the bar, having a transverse groove near the outer end thereof and a needle sleeve extending longitudinally therethrough, the groove bisecting the sleeve; and a clamp for securing each at least one arm at any desired position in the range.

11 Claims, 4 Drawing Figures

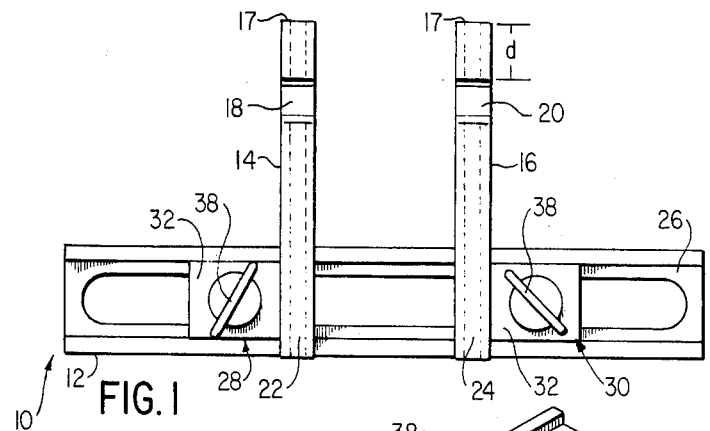
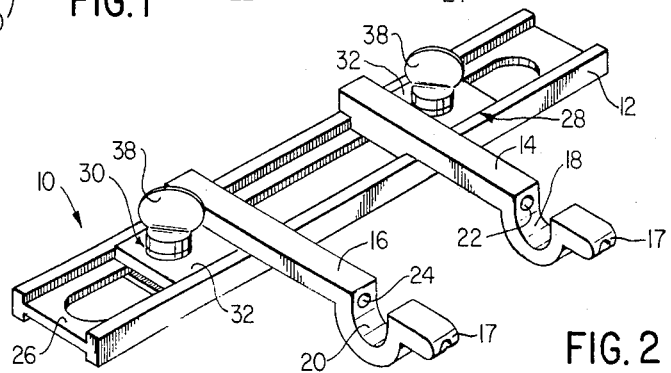
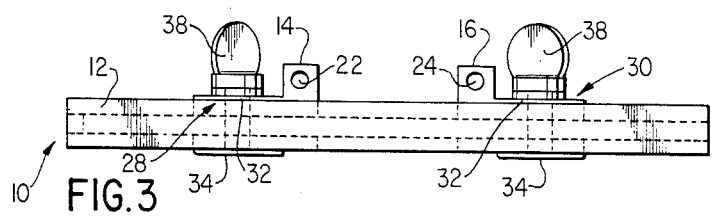
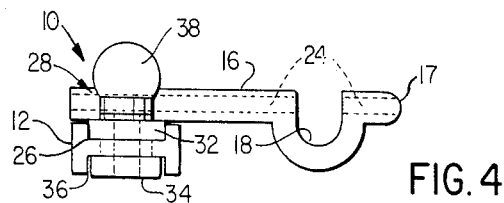

TENDON APPROXIMATOR

This application relates to a tendon approximator which is a surgical instrument utilized as an aid in rejoining severed tendons.

BACKGROUND OF THE INVENTION

There have heretofore been a number of problems associated with the rejoining of severed tendons, particularly in the case of smaller tendons such as those found in the hand. It has been necessary to grasp each of the severed ends of the tendon with forceps or hand held needles and to then hold the two ends together while suturing is accomplished. This method of proceeding includes a number of inherent disadvantages.

First, the working area in making such a repair is small, and this applies both in respect of the area of the severed tendon itself and of the operating theatre surrounding the patient. The current method of holding the tendon ends together with two forceps or hand held needles requires an additional assistant in the operating theatre and an additional pair of hands in the immediate vicinity of the tendon wound.

Second, increased handling of the tendon ends with the forceps can result in damage to the tendon and additional scar formation. The latter can adversely affect the gliding of the tendon after healing is completed.

Third, the manner of bringing the tendon ends together with forceps or hand held needles generally results in less than ideal positioning and thus leads to tension on the suture.

The present invention arose in an attempt to eliminate or reduce these disadvantages.

PRIOR ART

The applicant is unaware of any existing instrument which is intended for use in the manner of the present invention. As discussed above, the prior art procedures lacked completely an instrument of the nature of that of the invention.

SUMMARY OF THE INVENTION

An instrument has now been developed which allows the two ends of a severed tendon to be secured in the instrument and then manipulated to the correct anatomical position for suturing without tension.

The invention provides a tendon approximator comprising a slide bar, a pair of needle arms mounted on the slide bar, at least one of which is slidably mounted for movement over a range of positions on the slide bar, each arm comprising an elongated member extending outwardly from the bar, having a transverse groove near the outer end thereof and a needle sleeve extending longitudinally therethrough, the groove bisecting the sleeve; and means for securing each at least one arm at any desired position in the range.

BRIEF DESCRIPTION OF THE DRAWINGS

In drawings which illustrate embodiments of the invention,

FIG. 1 is a top plan view of an instrument according to the invention;

FIG. 2 is a perspective view of an instrument according to the invention;

FIG. 3 is a side elevation of an instrument according to the invention, and

FIG. 4 is an end elevation of an instrument according to the invention.

While the invention will be described in conjunction with an illustrated embodiment, it will be understood that it is not intended to limit the invention to such embodiment. On the contrary, it is intended to cover all alternatives, modifications and equivalents as may be included within the spirit and scope of the invention as defined by the appended claims.

DETAILED DESCRIPTION OF THE PREFERRED EMBODIMENT

In the following description, similar features in the drawings have been given similar reference numerals.

The tendon approximator 10 comprises a slide bar 12 on which are slidably mounted a pair of needle arms 14 and 16. The needle arms 14 and 16 are curved or otherwise formed to include transverse grooves 18 and 20 toward the outer end of the arms. A pair of needle sleeves 22 and 24 extend longitudinally through the needle arms 14 and 16 and are bisected by grooves 18 and 20.

At least one and preferably both of the needle arms are slidable in a guideway 26 in the slidebar 12. Means are provided, preferably in the form of clamps 28 and 30 adjusted by thumb screws 38, to secure the needle arms 14 and 16 at any desired position along the guideway 26. In the preferred case the needle arms are integral with clamps 28 and 30.

Various types of clamps can be utilized in the invention. For example, spring-loaded clamps loosed by the application of finger pressure could be utilized. However, the preferred form for clamps 28 and 30 comprises in each case a pair of sliding blocks 32 and 34 in respective upper and lower guideways 26 and 36, the latter on the underside of slide bar 12. The block 34 is threaded to receive the threaded thumb screw 38.

In the preferred case the needle arms 14 and 16 are integral with or secured to the blocks 32. The clamps 28 and 30 are substantially on opposite sides of respective arms 14 and 16 to allow the arms to be moved into close proximity with each other without interference.

Accordingly, the needle arms 14 and 16 can be positioned where required along the slide bar 12 by manipulation of the clamps 28 and 30 by means of the thumb screws 38.

The procedure in which the approximator is used is as follows. The approximator is placed in the wound with the slidebar 12 on the opposite side of the wound from the user. One of the tendon ends is placed in one of the grooves 18 or 20 with the severed end of the tendon toward the opposite groove. A needle is introduced into the corresponding needle arm 14 or 16, entering the sleeve at the end thereof adjacent the slide bar 12. The needle is inserted until it passes through the tendon in the groove 18 or 20 and on into that portion of the needle sleeve beyond the groove. The tendon end is then effectively skewered in the groove in one arm of the approximator.

This procedure is then repeated with the other severed end of the tendon in the second needle arm.

The two arms are then moved along the slide bar as required to place the two tendon ends in an anatomically correct position. The tendon ends are now ready to be sutured together. When the facing side of the tendon ends has been sutured together, the approximator 10 can simply be rotated 180° to expose the backside of the tendon and the suturing can be completed on that side. The needles are then extracted and the procedure is complete.

With particular reference to repair of tendons of the hand, a preferred set of dimensions can be established for the parts of the approximator. Thus, the slide bar 12 may be approximately 50 millimeters in length and about 6 millimeters in width. The needle arms 14 and 16 are preferably about 25 millimeters in length, the grooves 18 and 20 about 4 millimeters in diameter and the distance from the outside edge of the grooves to the outer end of the arms 14 and 16 about 3 millimeters. The arms are about 3 millimeters in width and the diameter of the needle sleeve is about 1.5 mm. These dimensions of the arms allow the use of a 22 gauge needle of about 25 millimeters in length. The sharp end of the needle will thus not extend beyond the ends 17 of the arms 14 and 16 and will thus not damage surrounding tissue.

The relatively short distance "d" from the outer edge of the grooves 18 and 20 to the outer ends 17 of the needle arms 14 and 16 is relatively small to facilitate the flipping over of the approximator to expose the backside of the tendon to complete the suturing. As well, these sleeve ends are preferably rounded for the same reason.

Clearly the dimensions can be varied depending on the particular application for which the device is intended.

Thus it is apparent that there has been provided in accordance with the invention a tendon approximator that fully satisfies the objects, aims and advantages set forth above. While the invention has been described in conjunction with a specific embodiment thereof, it is evident that many alternatives, modifications and variations will be apparent to those skilled in the art in light of the foregoing decription. Accordingly, it is intended to embrace all such alternatives, modifications and variations as fall within the spirit and broad scope of the invention.

What I claim as my invention:

1. A tendon approximator comprising:
   a slide bar;
   a pair of needle arms mounted on said slide bar, at least one of which is slidably mounted for movement over a range of positions on said slide bar, each said arm comprising an elongated member extending outwardly from said bar, having a transverse groove near the outer end thereof and a needle sleeve extending longitudinally therethrough, said groove bisecting said sleeve; and
   means for securing each said at least one arm at any desired position in said range.

2. The approximator of claim 1 in which said needle arms are substantially parallel.

3. The approximator of claim 1 in which both said needle arms are slidably mounted on said slide bar.

4. The approximator of claim 3, in which said grooves are so located that they can be brought into proximity by sliding movement of said arms on said slide bar.

5. The approximator of claim 3 in which said grooves lie on a common axis.

6. The approximator of claim 3 in which said means for securing comprises for each said arm a screw clamp.

7. The approximator of claim 4 in which one said screw clamp is integral with each said arm.

8. The approximator of claim 3 in which the diameter of said transverse groove is approximately 4 millimeters.

9. The approximator of claim 3 in which the diameter of said needle sleeve is approximately 1.5 millimeters.

10. The approximator of claim 1 in which the said arms are approximately 25 millimeters in length and the outer edges of said grooves are about 3 millimeters from the outer ends of said arms.

11. A tendon appproximator comprising:
    a slide bar;
    two parallel needle arms slidably mounted on said slide bar, each said arm comprising an elongated member extending outwardly from said bar, having a transverse groove near the outer end thereof and a needle sleeve extending therethrough, said grooves lying on a common axis and bisecting respective ones of said sleeves; and
    a pair of screw clamps for securing respective ones of said arms at preselected positions on said slide bar.

* * * * *